United States Patent [19]

Nagler et al.

[11] Patent Number: 5,891,879
[45] Date of Patent: Apr. 6, 1999

[54] QUINAZOLINONE-CONTAINING PHARMACEUTICAL COMPOSITIONS AND METHODS FOR THE USE THEREOF

[75] Inventors: Arnon Nagler; Shimon Slavin, both of Jerusalem; Israel Vlodavsky, Mevaseret Zion; Mark Pines, Rehovot, all of Israel

[73] Assignees: Hadasit Medical Research Services & Development Co., Inc., Jerusalem; Agricultural Organization Ministry of Agriculture State of Israel, Bet Dagan, both of Israel

[21] Appl. No.: 722,046

[22] PCT Filed: Aug. 29, 1995

[86] PCT No.: PCT/US95/11186

§ 371 Date: Dec. 9, 1996

§ 102(e) Date: Dec. 9, 1996

[87] PCT Pub. No.: WO96/06616

PCT Pub. Date: Mar. 7, 1996

[30] Foreign Application Priority Data

Aug. 31, 1994 [IL] Israel ........................ 110831

[51] Int. Cl.[6] .................................................. A61K 31/505
[52] U.S. Cl. ............................................................ 514/259
[58] Field of Search ................................................ 514/259

[56] References Cited

U.S. PATENT DOCUMENTS 5,449,678  9/1995  Pines et al. .......................... 514/259

OTHER PUBLICATIONS

Granot et al, Biochimica et Biophysica Acta, vol. 1156 pp. 107–112 1993.
Lindner et al. Circulation Research, vol. 68 (1), pp. 106–113 1991.

Primary Examiner—Rebecca Cook
Attorney, Agent, or Firm—Steinberg, Raskin & Davidson, P.C.

[57] ABSTRACT

The invention provides a pharmaceutical composition for preventing restenosis by the inhibition of vascular smooth muscle cell proliferation, comprising a compound of formula I:

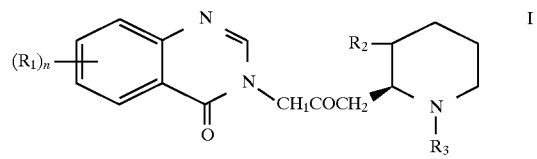

wherein: n=1 or 2

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl as active ingredient therein, and the physiologically acceptable salts thereof, in combination with a pharmaceutically acceptable carrier.

7 Claims, 8 Drawing Sheets

—□— CONTROL    —◆—0.075 μg/ml    —■—0.1 μg/ml    —○—0.125 μg/ml

—□— CONTROL    —◆—0.075μg/ml    —■—0.1 μg/ml    —○—0.125μg/ml
MEDIUM CHANGE A

QUINAZOLINONE-CONTAINING PHARMACEUTICAL COMPOSITIONS AND METHODS FOR THE USE THEREOF

This is a 371 of PCT/US95/11186 filed Aug. 29, 1995.

The present invention relates to compositions containing quinazolinones. More particularly, the present invention relates to a composition for the inhibition of restenosis, comprising a qunazolinone derivative as herein defined as active ingredient therein.

BACKGROUND OF THE INVENTION

In U.S. Pat. No. 3,320,124, issued in 1967, there is described and claimed a method for treating coccdidiosis with quinazolinone derivatives.

Halogufinone, otherwise known as 7-bromo-6-chloro-3-[3-(3-hydroxy-2-piperidinyl)-2-oxopropyl]-4(3H)-quinazolinone, was first described and claimed in said patent by American Cyanamid Company, and was the preferred compound taught by said patent and the one commercialized from among the derivatives described and claimed therein.

Subsequently, U.S. Reissue Pat. No. 26,833 and U.S. Pat. Nos. 4,824,847; 4,855,299; 4,861,758 and 5,215,993 all relate to the coccidiocidal properties of halofuginone, while U.S. Pat. No. 4,340,596 teaches that it can also be used for combatting theileriosis.

In U.S. Pat. No. 5,449,678, there is described and claimed an anti-fibrotic composition, comprising an amount of a compound of formula I:

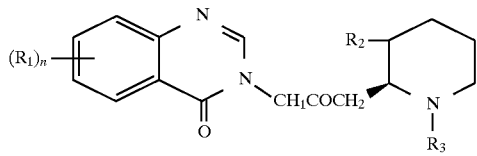

wherein: n 1 or 2

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl;

effective to inhibit collagen type I synthesis, as active ingredient therein, and the physiologically acceptable salts thereof.

After further research and development, it has now been discovered that the above-identified compounds of formula I are effective in the inhibition of restenosis, which formally is not a fibrotic condition.

The pathogenesis of atherosclerosis involves abnormal migration and proliferation of smooth muscle cells (SMCs) infiltrated with macrophages and embedded in extracellular matrix (ECM) of adhesive glycoproteins, proteoglycans and collagens [V. Fuster, et al., "The Pathogenesis of Coronary Artery Disease and the Acute Coronary Syndromes," *New Eng. J. Med.*, Vol. 326, pp. 242–250 (1992); R. Ross, "The Pathogenesis of Atherosclerosis: A Perspective for the 1990's," *Nature*, Vol. 362, pp. 801–809 (1993)]. Under physiological conditions, the majority of arterial SMCs remains in the Go phase and cell growth is controlled by a balance between endogenous proliferation-stimulating and proliferation-inhibiting factors. Following endothelial cell perturbation due to atherogenic risk factors (i.e., hypertension, hyperlipoproteinemia, diabetes mellitus), platelets and non-platelet-derived growth factors and cytokines are released and stimulate monocyte and SMC migration as well as SMC proliferation (V. Fuster, et al., ibid.; R. Ross, ibid.). Among these growth factors are platelet-derived growth factor (PDGF) [G. A. A. Ferns, et al., "Inhibition of Neoinitmal Smooth Muscle Accumulation after Angioplasty by an Antibody to PDGF," *Science*, Vol. 253, pp. 1129–1132 (1991)], basic fibroblast growth factor (bFGF) [V. Lindner, et al., "Role of Basic Fibroblast Growth Factor in Vascular Lesion Formation," *Circ. Res.*, Vol. 68, pp. 106–113 (1991)], and interleukin-1 (IL-1) [H. Loppnow and P. Libby, "Proliferating or Interleukin-1 Activated Human Vascular Smooth Muscle Cells Secrete Copious Interleukin 6, " *J. Clin. Invest.*, Vol. 85, pp. 731–738 (1990)]. Macrophages and platelets also release enzymes, i.e., elastase, collagenase, heparanase) that digest various constituents of the ECM and release bFGF and possibly other growth factors (TGFB) that are stored in basement membranes and ECM [I. Vlodavsky, et al., "Extracellylar Matrix-bound Growth Factors, Enzymes and Plasma Proteins," in: *Molecular and Cellular Aspects of Basement Membranes, Monographs in Cell Biology*, D. H. Rohrbach and R. Timpl, Eds., Academic Press, New York, N.Y., U.S.A., pp. 327–346 (1993)]. A potent growth-promoting activity towards SMCs is also exerted by thrombin, which, under certain conditions, may be present within the vessel wall [R. Bar-Shavit, et al., "Thrombin Immobilized to Extracellular Matrix Is a Mitogen for Vascular Smooth Muscle Cells: Non-Enzymatic Mode of Action," *Cell Reg.*, Vol. 1, pp. 453–463 (1990); S. M. Schwartz, "Serum-Derived Growth Factor is Thrombin?" *J. Clin. Invest.*, Vol 91, p. 4 (1993)]. Molecules that interfere with the growth-promoting activity of these growth factors may attenuate the progression of the atherogenic process.

Proliferation of arterial smooth muscle cells (SMC) in response to endothelial injury is a basic event in the process of restenosis of coronary arteries after percutaneous transluminal coronary angioplasty (PTCA) [V. Fuster, et al., ibid.]. Coronary bypass surgery or angioplasty are applied to reopen coronary arteries that have been narrowed by heart disease. A major problem with both procedures is that arteries rapidly reclog in about 30% of patients undergoing angioplasty and about 10% of bypass surgery patients. Vascular SMC are ordinarily protected by the smooth inner lining of the arteries, composed of vascular endothelial cells. However, following bypass surgery or angioplasty, SMC are often left exposed. In a futile effort to repair the wound, the cells proliferate and clog the artery.

SUMMARY OF THE INVENTION

According to the present invention, there is now provided a pharmaceutical composition comprising a compound of formula I as hereinbefore defined, in a pharmaceutically effective amount for preventing restenosis by the inhibition of vascular smooth cell proliferation and in combination with a pharmaceutically acceptable carrier.

In preferred compositions of the present invention, said compound is halofuginone.

The invention further encompasses a pharmaceutical composition as hereinabove described, wherein the carrier is a liquid and the composition is a solution.

In the practice of the invention, the amount of halofuginone incorporated in the pharmaceutical composition may vary widely. Factors considered when determining the precise amount are well-known to those skilled in the art.

Examples of such factors include, but are not limited to, the subject being treated, the specific pharmaceutical carrier, route of administration being employed, and the frequency with which the composition is to be administered.

As stated above, the compounds of the present invention are administered in a pharmaceutical composition which comprises the compound and a pharmaceutically acceptable carrier. As used herein, the term "pharmaceutically acceptable carrier" encompasses any of the standard pharmaceutically accepted carriers, such as a phosphate-buffered saline solution, water, emulsions such as an oil/water emulsion or a triglyceride emulsion and various types of wetting agents. An example of an acceptable triglyceride emulsion useful in the intravenous and intraperitoneal administration. of the compounds is the trighlyceride emulsion commercially known as Intralipid.

In the practice of the invention, the administration of the pharmaceutical composition may be effected by any of the well-known methods, including, but not limited to, intravenous, intraperitoneal, intramuscular, or subcutaneous administration.

While the invention will now be described in connection with certain preferred embodiments in the following examples and with reference to the appended figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars described are by way of example and for purposes of illustrative discussion of preferred embodiments of the present invention only, and are presented in the cause of providing what is believed to be the most useful and readily understood description of procedures as well as of the principles and conceptual aspects of the invention.

BRIEF DESCRIPTION OF THE DRAWINGS

The file of this patent contains at least one color photograph. Copies of this patent with color photograph(s) will be provided by the Patent and Trademark Office upon request and payment of the necessary fee.

In the drawings.

DETAILED DESCRIPTION OF THE INVENTION

EXAMPLES

1) Experimental Procedures

Cells

Figure 1:
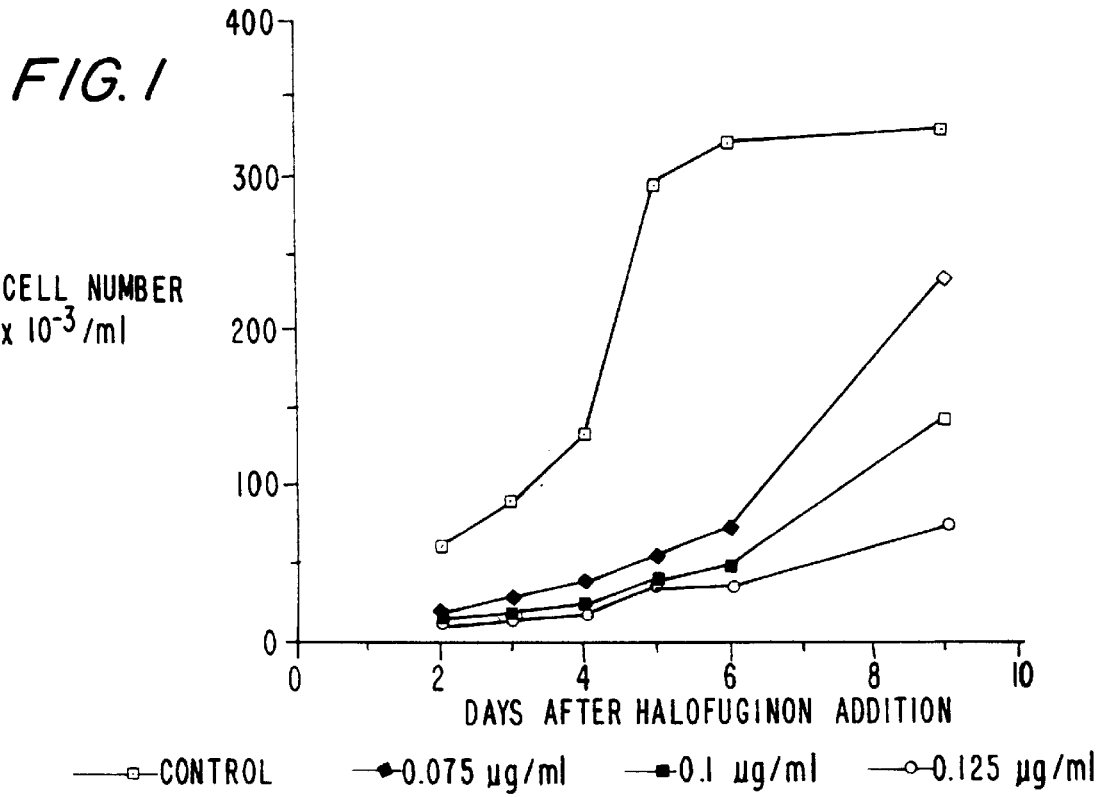
FIG. 1 is a characteristic curve showing the inhibitory effect of halofuginone on SMC proliferation.

SMC were isolated from the bovine aortic media as previously described [see, e.g., J. J. Castellot, et al., "Structural Determinants of the Capacity of Heparin to Inhibit the Proliferation of Vascular Smooth Muscle Cells: Evidence for a Pentasaccharide Sequence that Contains a 3-0-Sulfate Group," *J. Cell Biol.*, Vol. 102, pp. 1979–1984 (1986); and A. Schmidt, et al., "The Antiproliferative Activity of Arterial Heparan Sulfate Resides in Domains Enriched with 2-0-Sulfated Uronic Acid Residues," *J. Biol. Chem.*, Vol. 267, pp. 19242–19247 (1992)].

Briefly, the abdominal segment of the aorta was removed and the fascia cleaned away under a dissecting microscope. The aorta was cut longitudinally, and small pieces of the media were carefully stripped from the vessel wall. Two or three such strips, with average dimensions of 2–3 mm, were placed in 100 mm tissue culture dishes containing DMEM (4.5 g glucose/liter), supplemented with 10% FCS, 100 U/ml penicillin and 100 $\mu$g/ml streptomycin. Within 7–14 days, large patches of multilayered cells migrated from the explants. Approximately 1 week later, the cells were subcultured into 100-mm tissue culture plates (4–6×$10^5$ cells/plate). The cultures (passage 3-8) exhibited typical morphological characteristics of vascular SMC and the cells were specifically stained with monoclonal antibodies that selectively recognize the muscle form of actin (HF-35). This antibody does not recognize endothelial cells or fibroblasts.

Cultures of vascular endothelial cells were established from bovine aorta, as previously described by D. Gospodarowicz, et al. ["Clonal Growth of Bovine Endothelial Cells: Fibroblast Growth Factor as a Survival Agent," *Proc. Natl. Acad. Sci. U.S.A.*, Vol. 73, p. 4120 (1979)]. Stock cultures were maintained in DMEM (1 g glucose/liter) supplemented with 10% calf serum, 50 U/ml penicillin, and 50 $\mu$g/ml streptomycin at 37° C. in 10% $CO_2$ humidified incubators. Partially purified brain-derived bFGF (100 ng/ml) was added every other day during the phase of active cell growth [D. Gospodarowicz, et al., ibid., and I. Vlodavsky, et al., "Vascular Endothelial Cells Maintained in the Absence of Fibroblast Growth Factor Undergo Structural and Functional Alterations That Are Incompatible with Their In Vivo Differentiated Properties," *J. Cell Biol.*, Vol 83, pp. 468–486 (1979)].

Cell Proliferation; $^3$H-Thymidine Incorporation

SMCs were plated (4×$10^4$ cells/16 mm well) in DMEM supplemented with 10% FCS. 24 hours after seeding, the medium was replaced with medium containing 0.2% FCS, and 48 hours later, the cells were exposed to growth stimulants and $^3$H-thymidine (1 $\mu$Ci/well) for an additional 24–48 hours. DNA synthesis was assayed by measuring the radioactivity incorporated into trichloroacetic acid insoluble material [M. Benezra, et al., "Reversal of bFGF Autocrine Cell Transformation by Aromatic Anionic Compounds," *Cancer Res.*, Vol. 52, pp. 5656–5662 (1992)].

Growth Rate

SMCS (1.5×$10^4$ cells/well) were seeded into 24 well culture plates and exposed to growth stimulants as described above. 1 to 6 days after seeding, the cells were fixed with 2.5% formaldehyde in PBS. The plates were immersed in a bath of 0.1M borate buffer (pH 8.5), stained (1 h, 24° C.) with methylene blue (1% in 0.1M borate buffer, pH 8.5) and washed four times in water. This procedure removed practically all non-cell-bound dye. Specific cell incorporated methylene blue was dissolved with 0.5 ml of 0.1N HCl (1 h, 25° C.) and determined by measuring the absorbency at 620 nm (Bar-Shavit, et al., ibid.). The initial cell plating density was chosen to ensure a linear relationship between cell number and absorbance at the end of the experiment. In each experiment, 3 wells were fixed before adding the test compound to determine the initial average absorbance. This value was used to calculate doubling times (DT) of control and drug-treated cells, using the following equation:

$$DT = ln2/lN[(OD_t/OD_c)/h]$$

wherein:

DT=doubling time in hours;

$OD_t$=optical density of a test well at the end of the experiment;

$OD_c$=optical density of a control well at the beginning of the experiment;

h=duration of incubation in hours

The growth rate was calculated by dividing the doubling time of drug-treated cells by that of control cells [A. Horowitz, et al., "In Vitro Cytotoxicity of Liposome-Encapsulated Doxorubicin: Dependence on Liposome Composition and Drug Release," *Biochim. Biophys. Acta*, Vol. 1109, pp. 203–209 (1992)].

Cell Number

SMCs were seeded (2.5×10³ cells/well) into 24-well plates in DMEM (4.5 g glucose/liter), supplemented with 10% FCS and allowed to attach for 6 hours [A. Schmidt, et al., "The Antiproliferative Activity of Arterial Heparan Sulfate Resides in Domains Enriched with 2-0-Sulfated Uronic Acid Residues," *J. Biol. Chem.*, Vol. 267, pp. 19242–19247 (1992)]. The medium was removed and experimental medium (with or without halofuginone) containing 10% FCS was added to quadruplicate wells. After 4 days of incubation, the cell number was determined, using a Coulter counter (Schmidt, et al., ibid.). The degree of inhibition was calculated from the following formula:

% Inhibition=1-net growth in presence of halofuginone/net growth in control×100

The net growth was determined by subtracting the initial cell number from the final cell number.

2) Experimental Results i) Antiproliferative Effect of Halofuginone toward Vascular SMC Growth Rate Sparsely seeded vascular SMC were exposed to 10% FCS in the absence and presence of increasing concentrations of halofuginone. The cells were dissociated with STV and counted daily. As shown in FIG. 1, 80–90% inhibition of SMC proliferation was obtained in the presence of 75 ng/ml halofuginone, with an almost complete inhibition at 125 ng/ml.

Figure 2:
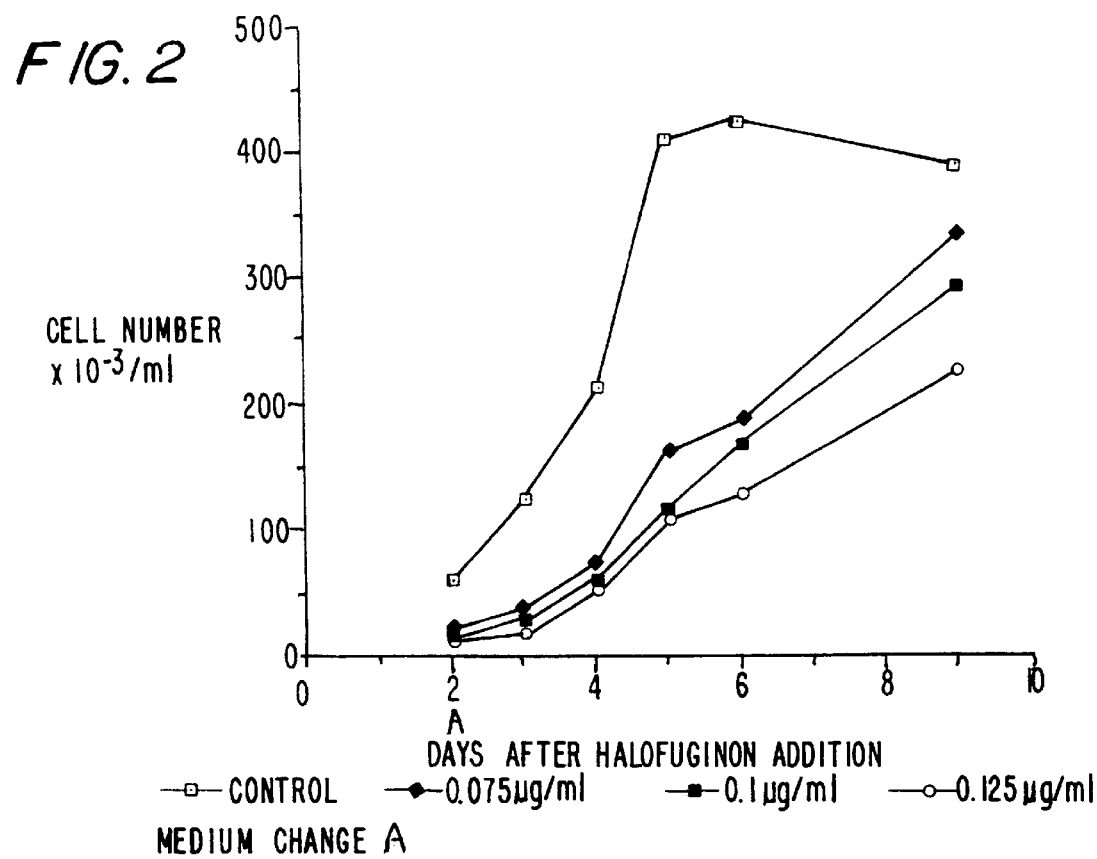
FIG. 2 is a characteristic curve showing reversion of the antiproliferative effect of halofuginone on SMC.

In another experiment, the SMCs were exposed to halofuginone for 48 hours, followed by removal of the drug and subsequent growth in regular growth medium. As demonstrated in FIG. 2, removal of the drug resulted in a gain of an accelerated growth rate similar to that of the untreated SMCs.

³H-Thymidine Incorporation

Figure 3A:
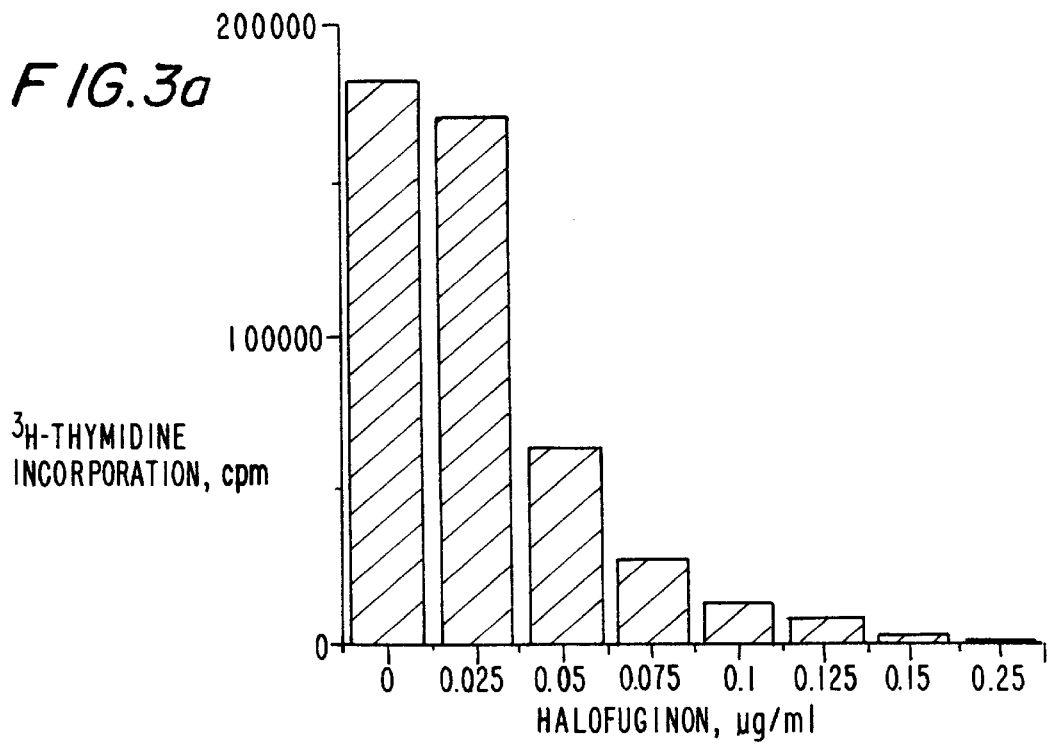
FIGS. 3a and 3b respectively are a bar graph and a characteristic curve, showing the effect of halofuginone on $^3$H-thymidine incorporation into vascular SMCS.
Figure 3B:
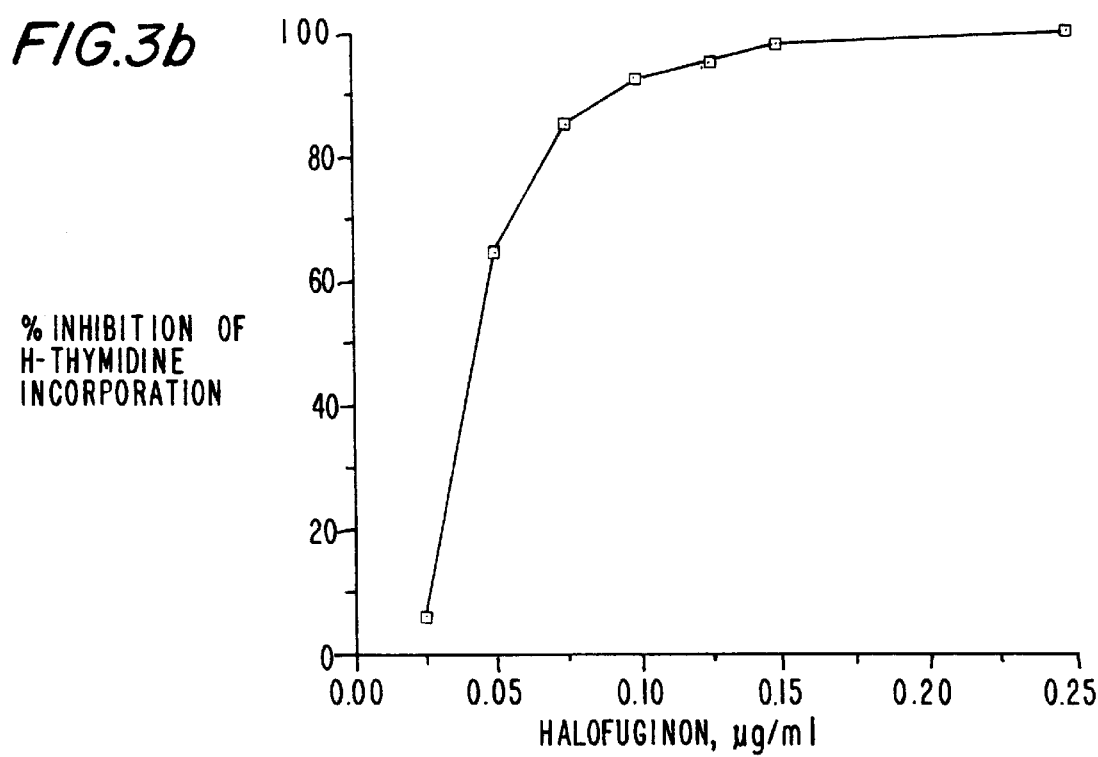
Figure 4:
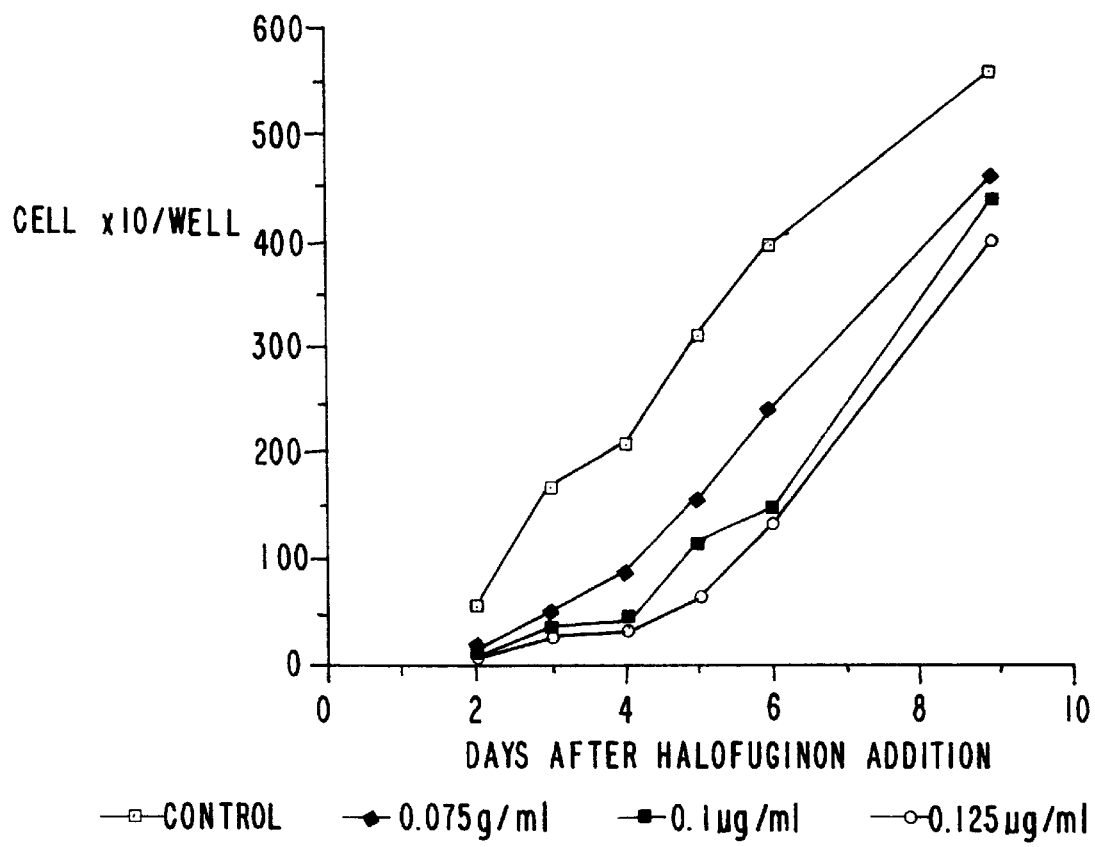
FIG. 4 is a characteristic curve showing the effect of halofuginone on vascular endothelial cell proliferation.
Figure 5A:
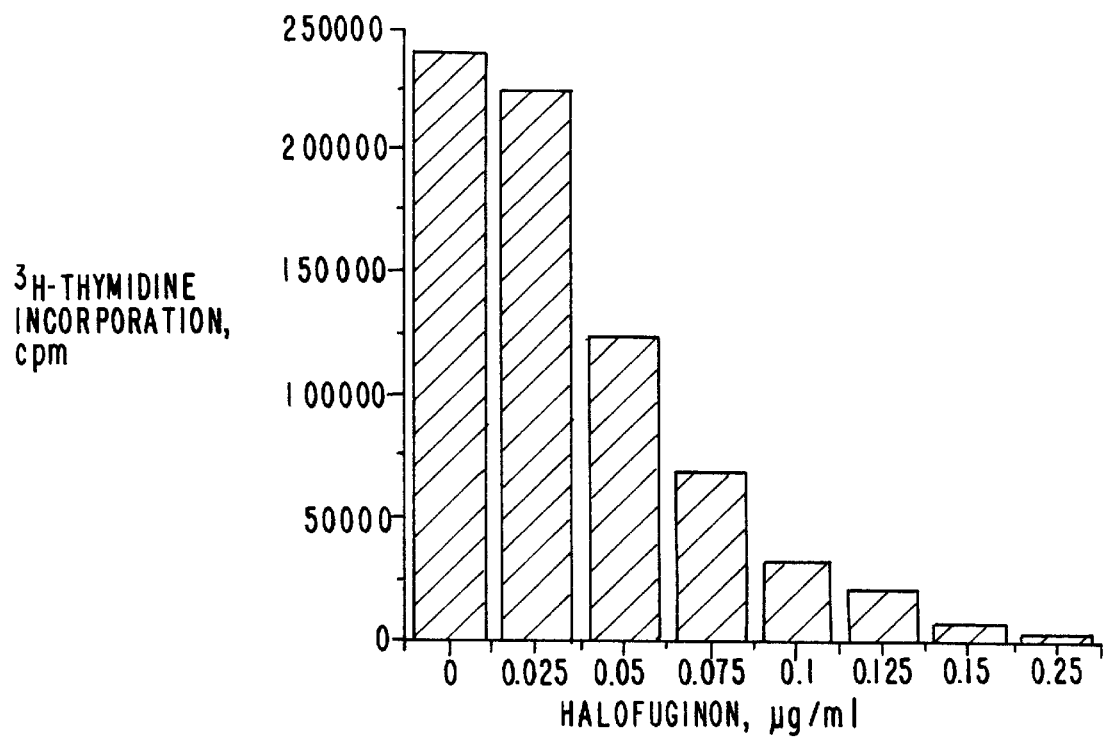
FIGS. 5a and 5b respectively are a bar graph and a characteristic curve, showing the effect of halofuginone on $^3$H-thymidine incorporation into vascular endothelial cells.
Figure 5B:
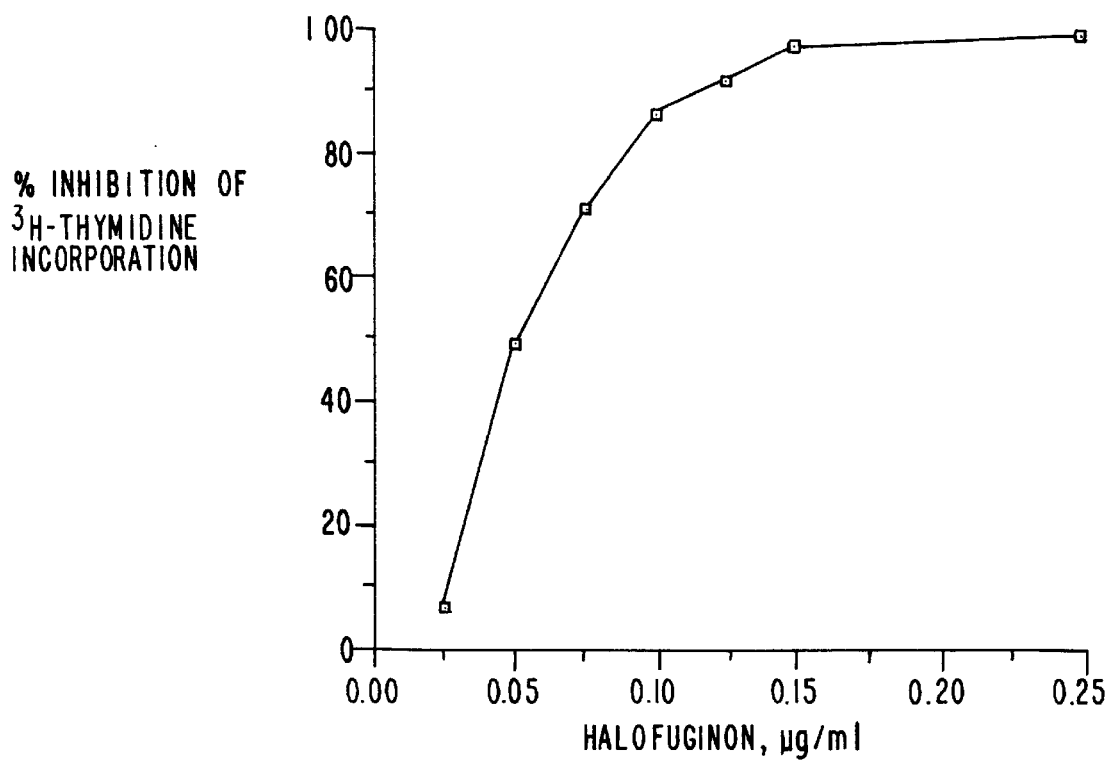

Subconfluent vascular SMCs maintained in a medium containing 10% FCS were exposed (48 hours, 37° C.) to ³H-thymidine in the absence and presence of increasing concentrations of halofuginone. As demonstrated in FIG. 3*a*, complete inhibition of DNA synthesis was observed at 0.15 μg/ml halofuginone, while 65% inhibition was obtained at a concentration as low as 0.05 μg/ml (FIG. 3*b*).

ii) AntiProliferative Effect toward Vascular Endothelial Cells and 3T3 Fibroblasts Vascular Endothelial Cells Sparsely seeded bovine aortic endothelial cells were cultured in medium containing 10% CS in the absence and presence of increasing concentrations of halofuginone. The cells were dissociated with 0.05% trypsin and 0.02% EDTA and counted daily. Inhibition of endothelial cell proliferation was observed primarily during the first 4 days, in cells treated with relatively high concentrations (0.1–0.125 μg/ml) of the drug (FIG. 4). Unlike the results with SMCs, the endothelial cells regained an almost normal growth rate (doubling time), starting on day 5 (FIG. 4), indicating that vascular EC are less susceptible than vascular SMCs to the inhibitory effect of halofuginone. Thymidine incorporation studies revealed a 50% inhibition of DNA synthesis at 0.05 μg/ml halofuginone (FIG. 5).

3T3 Fibroblasts

Figure 6:
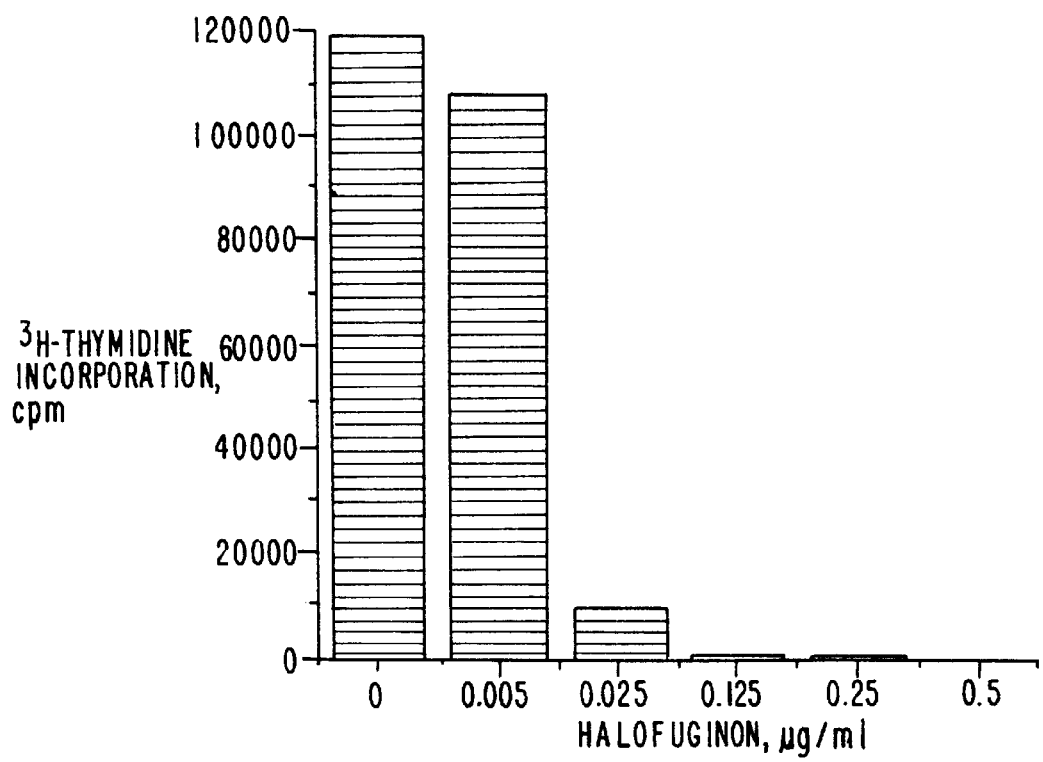
FIG. 6 is a bar graph showing antiproliferative effect of halofuginone on 3T3 fibroblasts.

FIG. 6 demonstrates that ³H-thymidine incorporation by actively growing 3T3 fibroblasts maintained in medium containing 10% FCS was almost completely inhibited in the presence of 0.025 μg/ml halofuginone, suggesting that fibroblasts are even more sensitive to the drug as compared to SMCs.

Effect on bFGF-Induced Cell Proliferation

Figure 7:
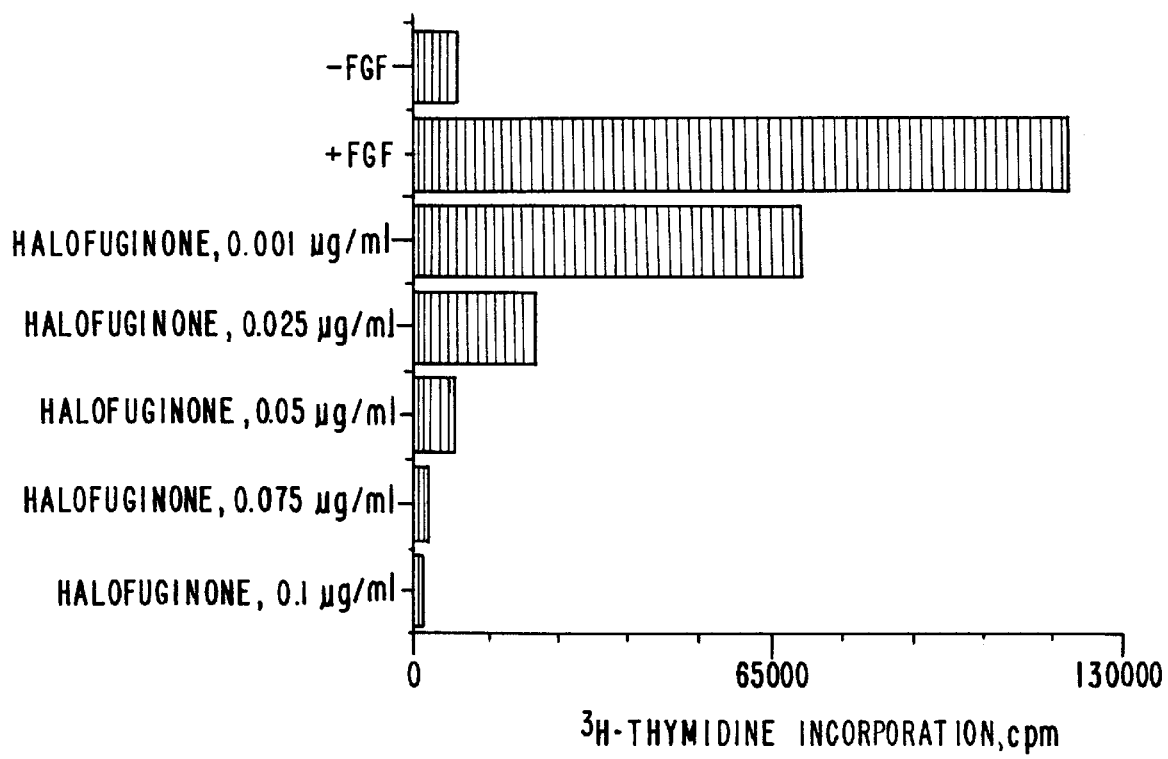
FIG. 7 is a bar graph showing the inhibitory effect of halofuginone on the mitogenic activity of bFGF.

Quiescent, growth arrested 3T3 fibroblasts maintained (48 hours) in medium containing 0.5% FCS are readily stimulated to proliferate by low concentrations at basic fibroblast growth factor (bFGF). Exposure to halofuginone (0.025 μg/ml) resulted in an almost complete inhibition of bFGF-stimulated thymidine incorporation in growth-arrested 3T3 fibroblasts (FIG. 7). This result suggests that halofuginone efficiently antagonizes the gorwth-promoting activity of bFGF.

iii) Arterial Stenosis Caused by Physical Injury

Adult New Zealand rabbits were anesthetized by intramuscular injection of ketamine (50 mg/kg). Physical injury was applied for 30 min. externally to the central artery of each ear [Banai, et al., *Circulation Res.*, Vol. 69, pp. 748–756 (1992)]. After the operation, the rabbits were housed in accordance with Animal Welfare Act specifications. Halofuginone (0.2 ml of 0.09 mg/ml) was introduced subcutaneously around the physical crush area 1 hour after the crush and once every 24 hours during the first 4 days. On day 14, the animals were sacrificed and the ears fixed in 10% buffered formaldehyde for 72 hours. The crush sites were further trimmed at 1 mm intervals, dehydrated in ethanol and xylene, and embedded in paraffin. Serial (5 μm) sections were stained by Movat pentachrome method. Computerized planimetry was performed at the site of the lesion and at an adjacent normal arterial segment displaced 2 mm from the location of the injury. Selection of the normal site was random; approximately one-half were proximal and one-half distal to the injury site. The lumen, the area cricumscribed by the internal elastic lamina ("original lumen") and the area circumscribed by the external border of the media (total vessel area) were traced, and the ratio between neointima and media was calculated. In all cases, the single section demonstrating the greatest extent of neointimal proliferation was selected for planimetry.

Figure 8A:
FIGS. 8a and 8b are color light micrographs of the central artery of a rabbit ear after being subjected to crush injury, respectively showing an untreated artery and an artery treated according to the present invention.
Figure 8B:
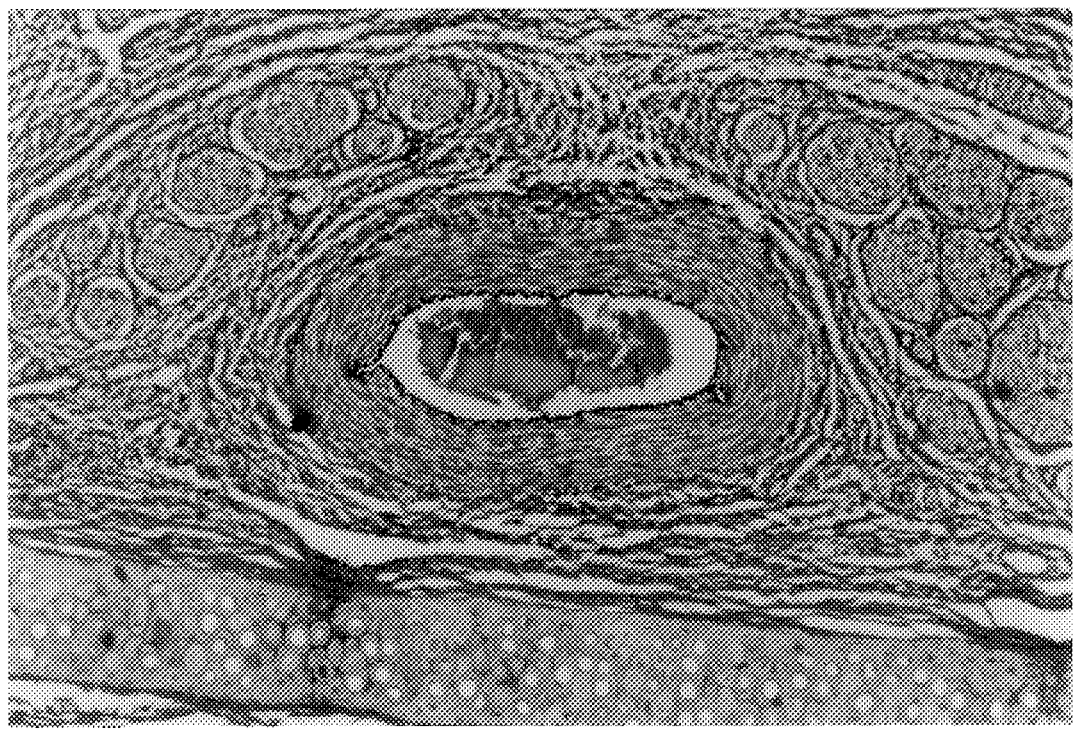

Referring now to FIGS. 8*a* and 8*b*, there are seen light micrographs of the central artery of a rabbit ear 14 days after external crush injury (Movat staining of representative cross-sections).

In FIG. 8a, the SMCs are migrating from the media into the neointima through the disrupted internal elastic lamina and the artery lumen is narrowed by the protruding neointima in the untreated artery. As can be seen, there is striking neointimal formation and an almost complete obliteration of the arterial lumen.

In contradistinction, in FIG. 8b there is seen a rabbit ear artery subjected to crush injury and treatment with halofuginone. An almost complete inhibition of neo-intimal formation is observed.

Figure 9:
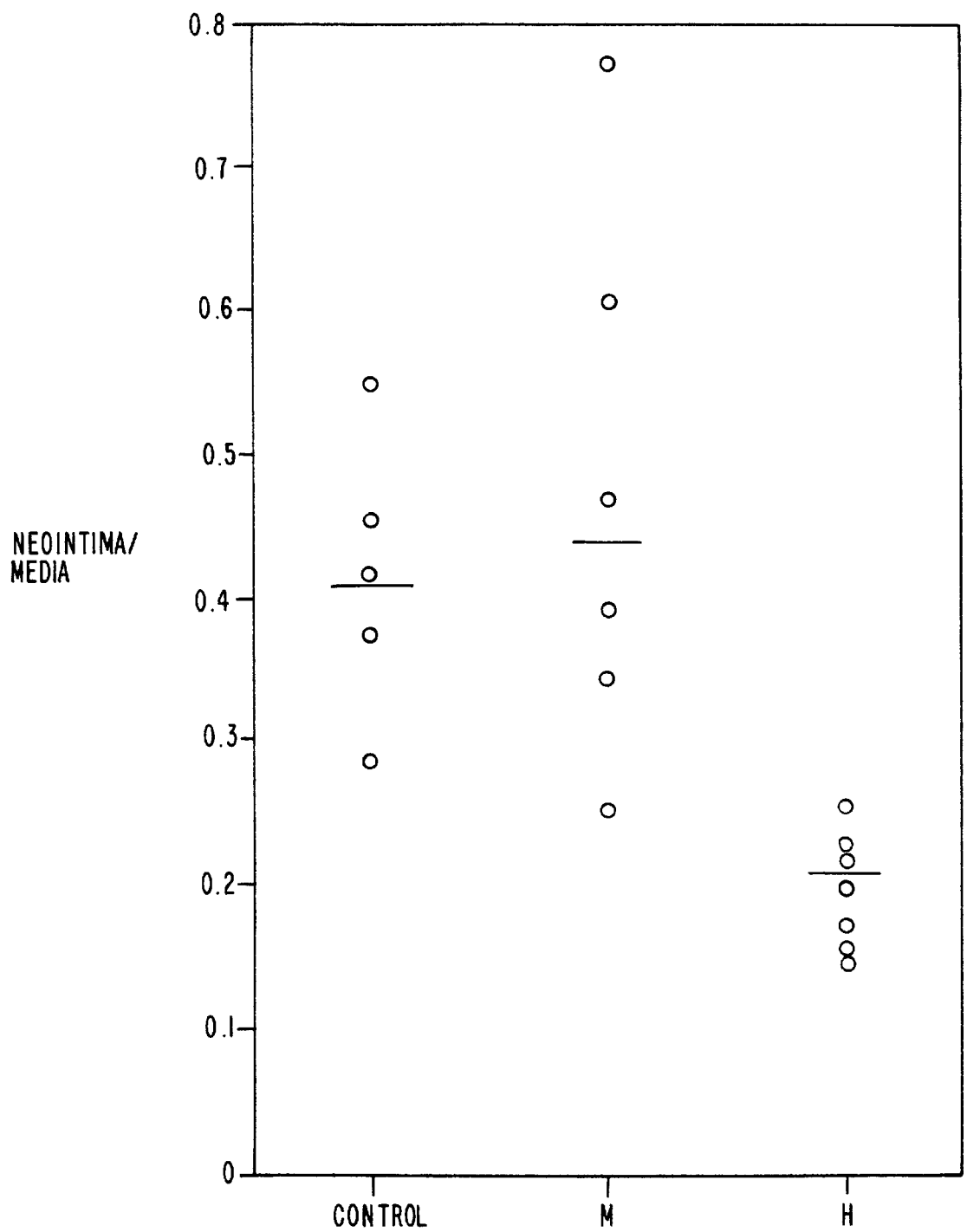
FIG. 9 is a graph showing the effect of halofuginone on injury-induced artery stenosis.

FIG. 9 shows a quantitative analysis of the ratio between enointima to media performed in control rabbits and rabbits treated with halofuginone (H) or a synthetic heparin-mimicking compound (M). Each point represents one rabbit.

Conclusions

Current approaches to inhibit the proliferation of vascular SMC utilize heparin, suramin, antibodies to various growth-promoting factors, anti-thrombin agents, and, most recently, antisense DNA technique. Heparin is a potent anticoagulant and its anti-proliferative activity is relatively small and subjected to major variations depending on the source and manufacturing company. Suramin is highly toxic at the effective dose, while antibodies are expensive, have a short half life and may elicit an immune response. Information on the antisense approach is new, and at present very limited.

The present invention, in its most preferred embodiment, utilizes a highly potent, inexpensive and non-toxic compound which inhibits the activity of various growth factors, including bFGF, and inhibits autocrine growth of vascular SMC and fibroblasts. Moreover, halofuginone is a low molecular weight compound which can be administered orally. The compound has been approved by the F.D.A. for use in farm animals. These characteristics make halofuginone a most promising clinically useful drug to inhibit restenosis.

Thus, the present invention provides for the use of halofuginone as a non-toxic compound that efficiently inhibits SMC proliferation, to provide an effective strategy for inhibiting the pathophysiology of arteriosclerosis, restenosis after coronary angioplasty, and neointimal proliferation in saphenous vein grafts.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for inhibiting restenosis by the inhibition of vascular smooth cell proliferation in a patient in need thereof, said method comprising administering to the patient a composition comprising a pharmaceutically effective amount of a compound of formula I:

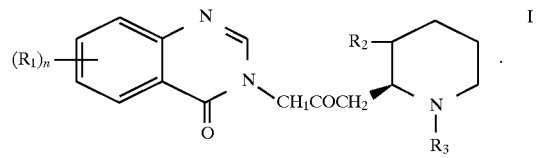

wherein:

n=1 or 2;

$R_1$ is a member of the group consisting of hydrogen, halogen, nitro, benzo, lower alky, phenyl and lower alkoxy;

$R_2$ is a member of the group consisting of hydroxy, acetoxy, and lower alkoxy, and $R_3$ is a member of the group consisting of hydrogen and lower alkenoxy-carbonyl;

as active ingredient therein, or a physiologically acceptable salt thereof, in combination with a pharmaceutically acceptable carrier.

2. A method according to claim 1, wherein said compound is halofuginone.

3. The method of claim 1, wherein said carrier is a liquid and said composition is a solution.

4. The method of claim 1, wherein said pharmaceutically acceptable carrier is selected from the group consisting of a phosphate-buffered saline solution, water, an emulsion and a wetting agent.

5. The method of claim 1, wherein said pharmaceutically acceptable carrier is a triglyceride emulsion.

6. The method of claim 1, wherein the mode of administration is selected from the group consisting of intravenous, intraperitoneal, intramuscular, or subcutaneous administration.

7. The method of claim 4, wherein the mode of administration is selected from the group consisting of intravenous and intraperitoneal administration.

* * * * *